United States Patent
Jones et al.

(10) Patent No.: US 6,291,713 B1
(45) Date of Patent: Sep. 18, 2001

(54) PROCESS OF TRANSFERRING α, β-UNSATURATED ALKYL GROUPS TO ELECTROPHILES

(75) Inventors: Philip Jones, Harlow (GB); Paul Knochel, Marburg (DE)

(73) Assignee: Metallgesellschaft Aktiengesellschaft, Frankfurt (DE)

( * ) Notice: Subject to any disclaimer, the term of this patent is extended or adjusted under 35 U.S.C. 154(b) by 0 days.

(21) Appl. No.: 09/404,665

(22) Filed: Sep. 23, 1999

(30) Foreign Application Priority Data

Oct. 9, 1998 (DE) .............................. 198 46 497

(51) Int. Cl.$^7$ ................................. C07C 211/00
(52) U.S. Cl. .......................... 564/391; 564/392; 568/715; 568/813; 568/822; 568/828; 568/832; 568/835
(58) Field of Search ..................................... 568/715, 813, 568/822, 828, 832, 835; 564/391, 392

(56) References Cited

PUBLICATIONS

Masanari et al, Tetrahedron Letters, 39(38), pp. 6903–6906, 1998.*

Kengo et al, Tetrahedron Letters, 34(47), pp. 7619–7622, 1993.*

* cited by examiner

*Primary Examiner*—Sreeni Padmanabhan
(74) *Attorney, Agent, or Firm*—Fulbright & Jaworski, LLP

(57) ABSTRACT

There is described a process of transferring α,β-unsaturated alkyl groups to an electrophile (aldehyde, ketone, nitrile, imine, alkyne) by means of a masked zinc alkyl in an aprotic solvent.

8 Claims, No Drawings

PROCESS OF TRANSFERRING α, β-UNSATURATED ALKYL GROUPS TO ELECTROPHILES

DESCRIPTION

The present invention relates to a process of transferring α,β-unsaturated alkyl groups (i.e. the allyl residue or substituted allyl residues or substituted and unsubstituted benzyl compounds) to electrophilic organic compounds subsequently referred to as electrophiles.

The transfer of allyl groups and allied residues to an organic molecule by means of organometallic reagents is a method of synthesis known for a long time. There are used for instance α,β-unsaturated alkyl compounds of magnesium, lithium or zinc. The same are generally prepared by reacting a metal with an unsaturated organohalogen compound. In this synthesis a certain amount of homocoupling product is formed in a secondary reaction by a so-called "Wurtz coupling":

2 M + ⟶ Hal ⟶ M + MHal

M = Li, Na, K
Hal = Cl, Br, I

M + ⟶ Hal ⟶ MHal

M = Mg, Zn
Hal = Cl, Br, I

The yield is thereby reduced and the processing and cleaning of the desired product is rendered more difficult.

The amount of homocoupling product (a 1,5-diene) depends on the nature of the metal and the specific reaction conditions. In general, a decrease in the reaction temperatures leads to an improved yield of organometal. However, low temperatures generally decrease the reaction rate and rarely are economic, as they can only be maintained by a high consumption of energy.

The transfer of compounds substituted in the allyl position to an electrophile constitutes a particular problem. In this case, an undesired rearrangement occurs in general by forming the thermodynamically more stable isomer substituted in the olefin position, so that product mixtures or only the resultant isomerization product are obtained:

R = alkyl
E = electrophile

In the "anionic" transfer of substituted allyl groups to an electrophile, poor regioselectivities are observed in general. For instance, when reacting E-2-butenyl zinc bromide with benzaldehyde a 1:1 mixture of the two diastereoisomers is obtained.

It is the object of the invention to eliminate the disadvantages of the prior art and create a process which allows to stereoselectively transfer α,β-unsaturated alkyl groups to an electrophile without isomerization.

This object is solved by the process indicated in claim 1. Claims 2 to 8 constitute a further development of the indicated process.

For transferring an α,β-unsaturated alkyl group (A)

(A)

there is used a zinc enolate (B) substituted in a sterically exacting way (i.e. $R^1$ and $R^2$ are voluminous substituents) or the zinc alkyl (C), which is in equilibrium with this zinc enolate and is reacted with an electrophile (E) to obtain the desired product (D):

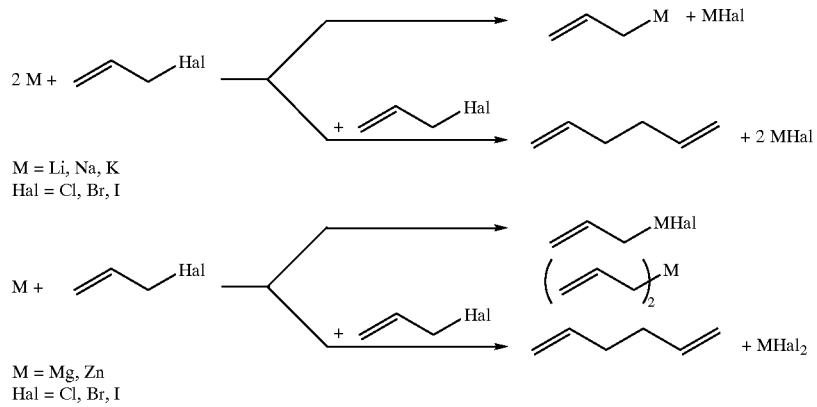

Wherein $$R^1 = \begin{array}{c} R' \\ | \\ -C-R'' \\ | \\ R''' \end{array}$$

with R'=H, alkyl and R"=alkyl and R'''=Alkyl,
$R^2 = R^1$ or phenyl, $R^3$, $R^4$ = independent of each other H, alkyl, aryl, heteroaryl, $R^5$ = H, alkyl, aryl, a functional group (ether, ester, nitrile, C=C double bond), $R^4$ and $R^5$ or $R^3$ and $R^5$ may be connected with each other via a cyclization, X=Cl, Br, J, alkyl or O—C($R^1$,$R^2$)—A and E=electrophile=aldehyde, ketone, nitrile, imine, alkyne.

The invention is based on the surprising observation that sterically exacting zinc enolates of the type (B) are not stable in contrast to the enolates of other metals, but fragment by forming a sterically exacting ketone and an allyl zinc compound (C). The system (B,C), subsequently referred to as "masked zinc alkyl", can react with an electrophile (E) by forming a valuable product (D).

The masked zinc alkyl (B,C) can be prepared by transmetallation of a compound (F), which includes the α,β-unsaturated alkyl group (A), in accordance with the following equation:

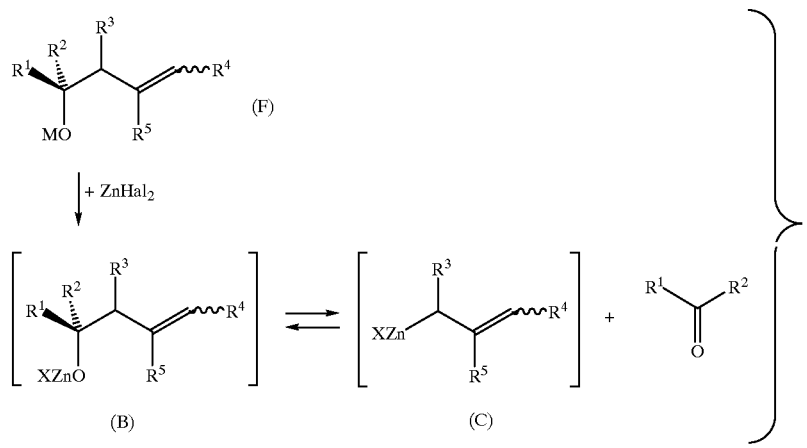

II

M = Li, Na, K, MgX and
Hal = Cl, Br, I

In general, the masked zinc alkyl (B,C) is not isolated, but formed in situ and immediately reacted with the electrophile (E).

Expediently, the molar ratio of the used metal enolate (F) to the electrophile (E) is largely stoichiometric (1:(0.8 to 3.0), preferably 1:(1.0 to 1.2), whereas the zinc salt $ZnHal_2$ can be used in an amount of 0.1 to 1.5 mol, based on 1 mol of the starting compound (F). An amount of 0.1 to 0.5 mol is preferred.

The metal enolate (F) can for instance be prepared in a known manner, as follows:

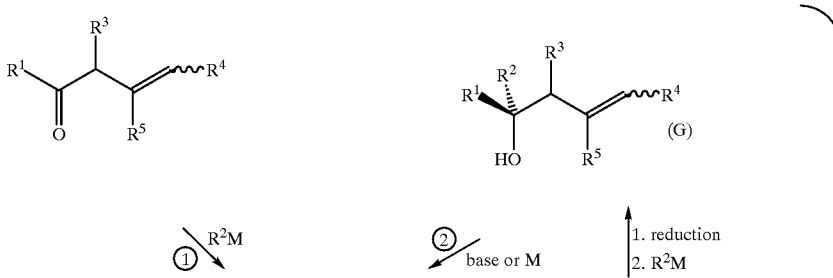

IV

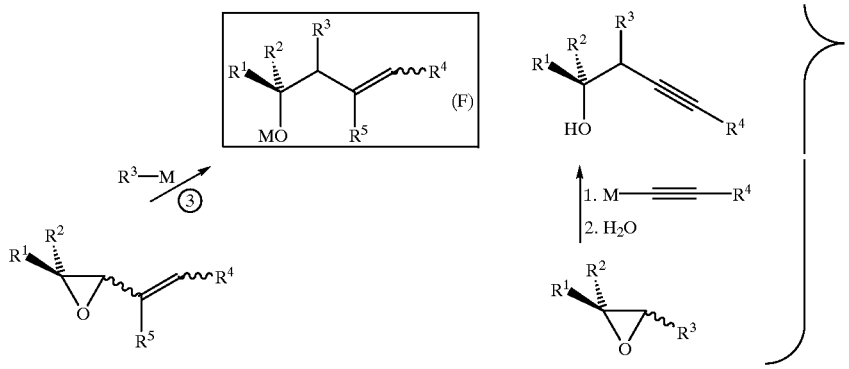

base = M—R$_6$ (R$^6$ = alkyl, aryl)
M = Li, Na, K, MgHal

The access to the metal enolate (F) most favorable for the individual case results for instance from the individual availability of the precursors.

The masked zinc alkyl (B,C) can also be prepared by metallation of a compound (G), which includes the α,β-unsaturated alkyl group (A), by means of a dialkyl zinc compound ZnR$_2$ in accordance with the following equation:

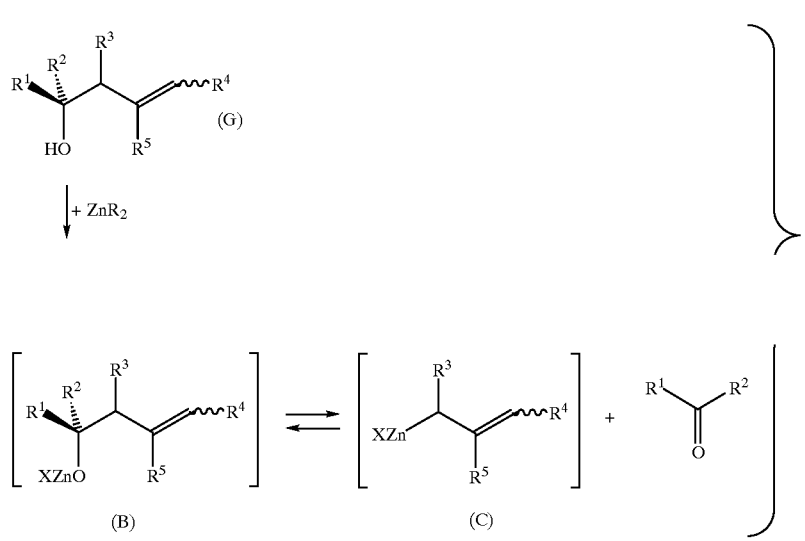

R = alkyl with 1 to 6 C atoms

This reaction can easily be performed e.g. with diethyl zinc.

With this process variant, too, the masked zinc alkyl (B,C) is generally not isolated, but formed in situ and immediately reacted with the electrophile (E).

All reactions described so far are performed in an aprotic solvent. As aprotic solvent there may be used ethers, amides or hydrocarbons or mixtures of these solvents. As ethers, there may for instance be used diethyl ethers, tetrahydrofuran (THF) or 2-methyl-THF, as amide there may for instance be used hexamethylphosphoric triamide (HMPT), N-methyl-2-pyrrolidinone (NMP), N,N-dimethylformamide (DMF) or 1,3-dimethyltetrahydro-2(1H)-pyrimidinone (DMPU), and as hydrocarbon there may for instance be used toluene, hexane, heptane or cyclohexane.

It was observed that the speed of the fragmentation (B)→(C) is influenced by the donor power of the solvent. The more polar the solvent, the faster the breakdown, i.e. the more the reaction temperature can be decreased. The second factor which determines the speed of the fragmentation is the specific substitution pattern of the zinc enolate (B). The following Table 1 indicates the respectively recommended temperature range for the allyl transfer reaction (I):

TABLE 1

| No. | Solvent | Substituent | | | | | Typical reaction temperature (° C.) | Typical reaction time |
|---|---|---|---|---|---|---|---|---|
| | | $R^1$ | $R^2$ | $R^3$ | $R^4$ | $R^5$ | | |
| 1 | THF/hexane | $^tBu$ | $^tBu$ | H | H | H | 0 to 40 | min - 2 hrs. |
| 2 | THF/hexane | $^iPr$ | $^iPr$ | H | H | H | 40 to 100 | 10 hrs. |
| 3 | THF/HMPT | $^iPr$ | $^iPr$ | H | H | H | 40 to 100 | 5 hrs. |
| 4 | THF/hexane | $^tBu$ | $^tBu$ | alkyl | H | H | −80 to −20 | min |
| 5 | THF/hexane | $^tBu$ | $^tBu$ | H | cyclo $C_4H_4$ | * | 40 to 100 | 5 hrs. |
| 6 | THF | $^tBu$ | $^tBu$ | H | alkyl | H | 20 to 100 | a few hours |
| 7 | THF | $^tBu$ | $^tBu$ | H | H | alkyl | 0 to 40 | a few hours |

* = benzyl ($R^3$ and $R^4$ are connected via cyclization), $^tBu$ = tert-butyl, $^iPr$ = iso-propyl When the masked zinc alkyl (B,C) is prepared from the alcohol precursor in accordance with reaction (III), there are basically no restrictions with respect to the residue R, but the more reactive zinc compounds with short-chain residues ($C_1$ to $C_4$) are preferred. Diethyl zinc, which is commercially available, is particularly recommended. The reaction is effected in strongly coordinating solvents (e.g. a mixture of THF and DMPU) at a temperature in the range between about 0 and 70° C. in the presence of the electrophile. Due to the low reactivity of dialkyl zinc compounds with respect to alcohols, the reaction takes a few to many hours.

On the other hand, the metal exchange in the reaction of metal elonates (F) with zinc halides in accordance with reaction (II) is much faster, so that even at low temperatures (e.g. −78° C.) short reaction times are observed. This variant is preferred as compared to the above-described mode of formation from alcohol and dialkyl zinc compound. This is particularly true for those α,β-unsaturated alkyl groups (A) and/or electrophiles (E) which can isomerize at higher temperatures in an undesired way.

The metal/zinc exchange (II) can accordingly be performed at temperatures which are adapted to the respective structures. The exchange preferably takes place in the presence of the electrophilic recipient molecule (E) by observing the reaction temperatures indicated in the above table. In the case of isomerization-stable α,β-unsaturated alkyl groups (A), the electrophile (E) can also be added upon termination of the metal/zinc exchange. For this case, however, the required reaction times are prolonged correspondingly.

A further advantage of the inventive process consists in that substituted allyl groups (A) ($R^3 \neq H$) can be transferred at low enough temperatures (e.g. −78° C.) with very good diastereoselectivities, and even at room temperature no isomerization occurs, whereas in the case of the direct, non-inventive addition of allyl zinc halides a ratio Anti:Syn of about 50:50 is obtained.

The subject-matter of the invention will subsequently be explained in detail with reference to embodiments.

EXAMPLE 1

Preparation of 1-phenyl-but-3-en-1-ol by transfer of the

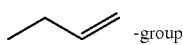-group to benzaldehyde with $R^1=R^2={}^tBu$ 1.94 ml of a 1.4-molar solution of n-butyllithium (2.71 mmol) in pentane were added dropwise at 0° C. under argon for 2 min to a stirred solution of 500 mg (2.71 mmol) 3-tert-butyl-2,2-dimethylhex-5-en-3-ol in 4 ml THF. The solution obtained was stirred for 15 minutes, and then a solution of 610 mg (2.71 mmol) $ZnBr_2$ in 2 ml THF and subsequently 275 μl (2.71 mmol) benzaldehyde were added. The reaction mixture was stirred for 1 hour and heated to room temperature. Subsequently, 15 ml $NH_4Cl$ solution were added. The organic components were extracted three times with 15 ml $Et_2O$ each, the combined organic phases were washed with 10 ml brine, then dried and concentrated under reduced pressure. The raw product obtained was cleaned by means of a silica column with 15% diethyl ether/light gasoline. There was obtained the alcohol as a colorless oil.

Yield: 356 mg (89%)

EXAMPLE 2

Preparation of 1-phenyl-but-3-en-1-ol by transfer of the

-group to benzaldehyde with $R^1=R^2={}^tBu$ by using an understoichiometric quantity $ZnBr_2$.

The reaction was performed analogous to Example 1 with 61 mg (0.27 mmol) $ZnBr_2$. There was obtained the alcohol as a colorless oil.

Yield: 368 mg (92%)

EXAMPLE 3

Preparation of 1-phenyl-but-3-en-1-ol by transfer of the

-group to benzaldehyde with $R^1=R^2={}^iPr$ 2.29 ml of a 1.4-molar solution of n-butyllithium (3.20 mmol) in pentane were added dropwise at 0° C. under argon for 2 minutes to a stirred solution of 500 mg (3.20 mmol) 2-methyl-3-isopropyl-hex-5-en-3-ol in 2 ml THF. The solution obtained was heated to room temperature, stirred for 15 minutes, and then a solution of 721 mg (3.20 mmol) $ZnBr_2$ in 2 ml THF and subsequently 330 μl (3.20 mmol) benzaldehyde and 6 ml HMPA were added. The reaction mixture was heated to 70° C. and stirred for 6 hours at this temperature. Subsequently, it was cooled to room temperature and processed analogous to Example 1. The raw product obtained was cleaned by means of a silica column with 15% diethyl ether/light gasoline. There was obtained the alcohol as a colorless oil.

Yield: 464 mg (98%)

EXAMPLE 4

Preparation of 1-phenyl-but-3-en-1-on by transfer of the

 -group to benzonitrile 1.94 ml of a 1.4 molar solution of n-butyllithium (2.71 mmol) in pentane were added dropwise at 0° C. under argon for 2 min to a stirred solution of 500 mg (2.71 mmol) 3-tert-butyl-2,2-dimethylhex-5-en-3-ol in 4 ml THF. The solution obtained was stirred for 15 minutes, a solution of 370 mg (2.71 mmol) $ZnCl_2$ in 2 ml THF and then 278 µl (2.71 mmol) benzonitrile were added. The reaction mixture was heated to room temperature and stirred for 1 hour. Subsequently, 15 ml of a 0.25-molar HCl solution and 30 ml $Et_2O$ were added, and the mixture obtained was vigorously stirred for 10 minutes. The phases were separated, the organic components were extracted twice from the aqueous phase with 15 ml $Et_2O$ each, the combined organic phases were washed with 10 ml brine, then dried and concentrated under reduced pressure. The raw product obtained was cleaned by means of a silica column with 5% diethyl ether/light gasoline. The ketone was obtained as a colorless oil.

Yield: 289 mg (73%)

EXAMPLE 5

Preparation of 1-allylcyclohexanol by transfer of the

 -group to cyclohexanone 1.94 ml of a 1.4-molar solution of n-butyllithium (2.71 mmol) in pentane were added dropwise at 0° C. under argon for 2 minutes to a stirred solution of 500 mg (2.71 mmol) 3-tert-butyl-2,2-dimethylhex-5-en-3-ol in 4 ml THF. The solution obtained was stirred for 15 minutes, and then a solution of 610 mg (2.71 mmol) $ZnBr_2$ in 2 ml THF and 280 µl (2.71 mmol) cyclohexanone were added. The reaction mixture was stirred for 4 hours and heated to room temperature. Subsequently, it was processed analogous to Example 1. The raw product obtained was cleaned by means of a silica column with 20% diethyl ether/light gasoline. There was obtained the alcohol as a colorless oil.

Yield: 325 mg (82%)

EXAMPLE 6

Preparation of (1-allyl-3-methyl-but-2-enyl) benzylamine by transfer of the

 -group to benzyl-(3-methyl-but-2-enylidene)amine

The reaction was performed analogous to Example 1 with 500 mg (2.71 mmol) 3-tert-butyl-2,2-dimethylhex-5-en-3-ol, 1.93 ml (2.71 mmol) of a 1.4-molar n-butyllithium solution in pentane, 468 mg (2.71 mmol) benzyl-(3-methyl-but-2-enylidene)amine and 370 mg (2.71 mmol) $ZnCl_2$. The raw product obtained was cleaned by means of a silica column with 25–100% diethyl ether/light gasoline. There was obtained the amine as a colorless oil.

Yield: 522 mg (90%)

EXAMPLE 7

Preparation of threo 2-methyl-1-phenyl-3-buten-1-ol by stereoselective transfer of the

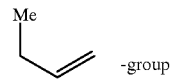 -group to benzaldehyde 1.58 ml of a 1.6-molar solution of n-butyllithium (2.52 mmol) in pentane were added dropwise at −78° C. under argon for 5 minutes to a stirred solution of 500 mg (2.52 mmol) 3-tert-butyl-2,2,4-trimethylhex-5-en-3-ol in 4 ml THF. The solution obtained was stirred for 15 minutes, then 256 µl (2.52 mmol) benzaldehyde and subsequently for 3 minutes a solution of 343 mg (2.52 mmol) $ZnCl_2$ in 2 ml THF were added. The reaction mixture was stirred for 1 hour at −78° C. and then heated to room temperature. Subsequently it was processed analogous to Example 1. The raw product obtained was cleaned by means of a silica column with 10% diethyl ether/light gasoline. There was obtained the alcohol as a pale-yellow oil.

Yield: 341 mg (83%), ratio Anti:Syn=94:6

EXAMPLE 8

Preparation of cis and trans 1-phenyl-3-heptene-1-ol proceeding from 2,2-di-tert-butyloxirane 1.26 ml (12.8 mmol) 1-pentyne were added dropwise at 0° C. under argon for 5 minutes to 8.0 ml (12.8 mmol) of a 1.6-molar n-butyllithium solution in pentane. The solution obtained was cooled for another 15 minutes, and then the solvent was withdrawn under reduced pressure. 5 ml HMPA and a solution of 1.0 g (6.4 mmol) 2,2-di-tert-butyloxirane in 2 ml HMPA were added. The reaction solution was stirred for 20 hours at room temperature. Subsequently, it was processed analogous to Example 1. The raw product obtained was cleaned by means of a silica column with 2% diethyl ether/light gasoline. There were obtained 1.21 g (84%) 3-tert-butyl-2,2-dimethylnon-5-in-3-ol

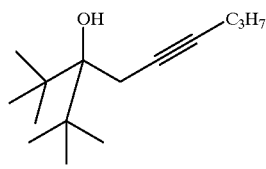

as a colorless oil.

50 mg of a catalyst of 5% palladium on barium sulfate were added at once to a stirred solution of 500 mg (2.23 mmol) 3-tert-butyl-2,2-dimethylnon-5-in-3-ol in 5 ml pyridine. The mixture obtained was degassed three times, exposed to a hydrogen atmosphere and stirred overnight. Subsequently, it was diluted with 100 ml pentane and filtered over silica gel. The silica gel was washed with 100 ml $Et_2O$. The combined organic phases were washed with a copper sulfate solution (5×100 ml), with $H_2O$ (100 ml) and with salt solution (50 ml), dried and concentrated under reduced pressure. There were obtained 503 mg (99%) (Z)-3-tert-butyl-2,2-dimethylnon-5-en-3-ol as a colorless oil.

The further reaction was performed analogous to Example 7 with 452 mg (2.0 mmol) (Z)-3-tert-butyl-2,2-dimethylnon-5-en-3-ol, 1.45 ml (2.0 mmol) of a 1.38-molar n-butyllithium solution in pentane, 202 µl (2.0 mmol) benzaldehyde and 272 mg (2.0 mmol) $ZnCl_2$. Upon heating to room temperature the reaction solution was stirred for 80 hours. The raw product obtained was cleaned by means of a silica column with 2–10% diethyl ether/light gasoline. There were first obtained 180 mg (40%) of the educt and then 197 mg (52%) of the product 1-phenyl-3-hepten-1-ol (mixture of the cis and trans isomers) as a colorless oil.

EXAMPLE 9

Preparation of 1,2-diphenyl-1-ethanol 1.33 ml of a 1.6-molar solution of n-butyllithium (2.13 mmol) in pentane were added dropwise at room temperature under argon for 2 minutes to a stirred solution of 500 mg (2.13 mmol) 3-benzyl-2,2,4,4-tetramethyl-3-pentanol in 4 ml THF. The solution obtained was stirred for 30 minutes, then 275 µl (2.13 mmol) benzaldehyde, 290 mg (2.13 mmol) $ZnCl_2$ and 2 ml HMPA were added. The reaction mixture was heated to 70° C. and stirred for 4 hours at this temperature. Subsequently, it was cooled to room temperature and processed analogous to Example 1. The raw product obtained was cleaned by means of a silica column with 35% diethyl ether/light gasoline. There was obtained the alcohol as a colorless oil.

Yield: 327 mg (78%)

EXAMPLE 10

Preparation of 2-methylene-pent-4-en-1-ol 3.9 ml of a 1.4-molar solution of n-butyllithium (5.4 mmol) in pentane were added dropwise at 0° C. under argon for 2 minutes to a stirred solution of 1.0 g (5.4 mmol) 3-tert-butyl-2,2-dimethylhex-5-en-3-ol in 8 ml THF. The solution obtained was stirred for 15 minutes, then 741 mg (5.4 mmol) $ZnCl_2$ and 347 mg (2.71 mmol) trimethylprop-2-inyloxysilane were added. The reaction mixture was heated to room temperature, stirred for 2 hours, poured into 10 ml of a 2-molar HCl solution and 10 ml $Et_2O$, stirred for another 15 minutes and processed analogous to Example 1. The raw product obtained was cleaned by means of a silica column with 25% diethyl ether/light gasoline. There was obtained the alcohol as a colorless oil.

Yield: 202 mg (74%)

What is claimed is:

1. A process of transferring α,β-unsaturated alkyl groups (A)

to an electrophile (E), characterized in that the α,β-unsaturated alkyl group (A) is transferred to the electrophile (E) by means of a masked zinc alkyl (B,C) according to the general equation I, wherein with R'=H, alkyl and R"=alkyl and R'"=Alkyl, $R^2=R^1$ or phenyl, $R^3$, $R^4$=independent of each other H, alkyl, aryl, heteroaryl, $R^5$=H, alkyl, aryl, a functional group (ether, ester, nitrile, C=C double bond), $R^4$ and $R^5$ or $R^3$ and $R^5$ may be connected with each other via a cyclization, X=Cl, Br, I, alkyl or O—C($R^1$,$R^2$)—A and E=electrophile=aldehyde, ketone, nitrile, imine, alkyne, and the reaction is performed in an aprotic solvent.

2. The process as claimed in claim 1, wherein the masked zinc alkyl (B, C) is prepared by transmetallation of a compound (F), which includes the α,β-unsaturated alkyl group (A), according to the general equation II

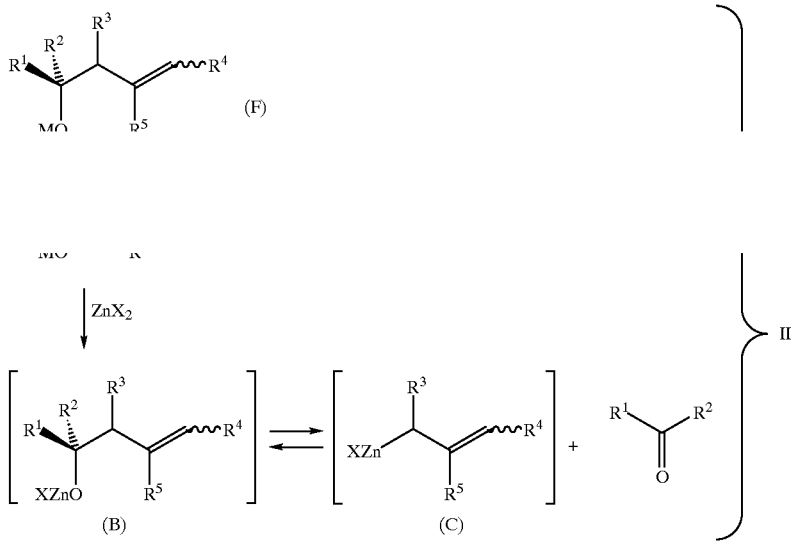

wherein
 M=Li, Na, K, or MgX,
 Hal=Cl, Br or I, and
 X=Cl, Br, I, or O—C(R$^1$,R$^2$)—A and the reaction is performed in an aprotic solvent.

3. The process as claimed in claim 2, wherein the compound (F), the zinc salt ZnHal$_2$, and the electrophile (E) are used in a molar ratio of 1:(0.1 to 1.5):(0.8 to 3.0).

4. The process as claimed in claim 2 wherein the zinc salt ZnHal$_2$, is used in an amount of 0.1 to 0.5 mol, based on 1 mol of the starting compound (F).

5. The process as claimed in claim 1, wherein the masked zinc alkyl (B, C) is prepared by the metallation of a compound (G) including the α,β-unsaturated alkyl group (A) by means of a dialkyl zinc compound ZnR$_2$=according to the general equation III

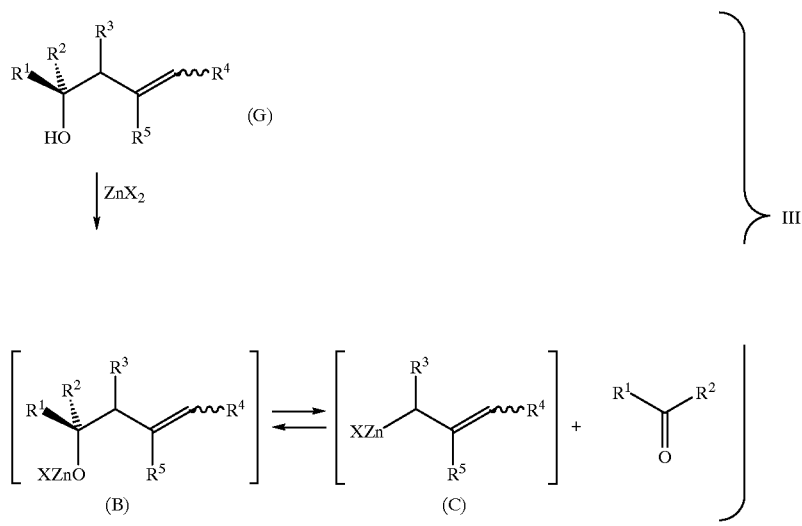

wherein

R=alkyl with 1 to 6 C atoms
X=R or O-13 C(R$^1$, R$^2$)—A and the reaction is performed in an aprotic solvent.

6. The process as claimed in claim 1, wherein the preparation of the masked zinc alkyl (B,C) and the reaction with the electrophile (E) are performed as a one-pot reaction.

7. The process as claimed in claim 1, wherein ethers, amides or hydrocarbons or mixtures of these solvents are used as aprotic solvent.

8. The process as claimed in claim 1, wherein as aprotic solvent there are used diethyl ether, tetrahydrofuran (THF), 2-methyl-THF, hexamethylphosphoric triamide (HMPT), N-methyl-2-pyrrolidinone (NMP), N,N-dimethylformamide (DMF), 1,3-dimethyltetrahydro-2(1H)-pyrimidinone (DMPU), toluene, hexane, heptane, cyclohexane or mixtures of these solvents.

* * * * *